United States Patent [19]
Jain et al.

[11] Patent Number: 5,888,497
[45] Date of Patent: Mar. 30, 1999

[54] AGAROSE COATED AGAROSE BEADS CONTAINING CANCER CELLS THAT PRODUCE MATERIAL WHICH SUPPRESSES CANCER CELL PROLIFERATION

[75] Inventors: Kanti Jain, New York, N.Y.; Albert L. Rubin, Englewood, N.J.; Shirin Asina, New York, N.Y.; Barry Smith, New York, N.Y.; Kurt Stenzel, New York, N.Y., .

[73] Assignee: The Rogosin Institute, New York, N.Y.

[21] Appl. No.: 745,063

[22] Filed: Nov. 7, 1996

Related U.S. Application Data

[63] Continuation-in-part of Ser. No. 625,595, Apr. 3, 1996, abandoned.

[51] Int. Cl.⁶ ............... A01N 63/00; C12N 11/10; C12N 5/06; C12N 5/08
[52] U.S. Cl. ............ 424/93.7; 435/178; 435/382; 435/395
[58] Field of Search .................... 435/174, 177, 435/178, 180, 182, 382, 395; 424/93.7

[56] References Cited

U.S. PATENT DOCUMENTS

| | | | |
|---|---|---|---|
| 4,352,883 | 10/1982 | Lim | 435/178 |
| 4,391,909 | 7/1983 | Lim | 435/178 |
| 4,409,331 | 10/1983 | Lim | 435/178 |
| 4,647,536 | 3/1987 | Mosbach et al. | 435/177 |
| 4,663,286 | 5/1987 | Tsang et al. | 435/178 |
| 4,673,566 | 6/1987 | Goosen et al. | 424/19 |
| 4,798,786 | 1/1989 | Tice et al. | 435/177 |
| 4,902,295 | 2/1990 | Walthall et al. | 623/11 |
| 4,971,833 | 11/1990 | Larsson et al. | 427/213.33 |
| 4,997,443 | 3/1991 | Walthall et al. | 623/11 |
| 5,053,332 | 10/1991 | Cook et al. | 435/178 |
| 5,227,298 | 7/1993 | Weber et al. | 435/178 |
| 5,643,569 | 7/1997 | Jain et al. | 424/93 |

FOREIGN PATENT DOCUMENTS

WO9601611  1/1996  WIPO .

OTHER PUBLICATIONS

Brodelius et al., "Entrapment of Plant Cells in Different Matrices", FEBS LEtters: 122(2): 312–316 (1980).

*Primary Examiner*—David M. Naff
*Attorney, Agent, or Firm*—Fulbright & Jaworski, LLP

[57] ABSTRACT

Implantable beads which contain agarose and optionally collagen, and are coated with agarose have incorporated within cells which produce diffusible biological products. The beads may be used as implants to modulate a recipient's immune response. The beads may also be used in an in vitro context to encourage specific types of cells to grow, to produce desirable products in culture, or to suppress growth of certain cells. The implants may also suppress growth of certain cells following administration to a subject. Cancer cells such as renal cancer cells when restricted by being entrapped in the beads produce more of a material that suppresses cancer cell proliferation.

8 Claims, No Drawings ic gel, such as agarose, followed by coating with further agarose, led to a product which did not cause fibrosis when administered to a subject, while permitting secretion of the product of interest into the subject.

AGAROSE COATED AGAROSE BEADS CONTAINING CANCER CELLS THAT PRODUCE MATERIAL WHICH SUPPRESSES CANCER CELL PROLIFERATION

RELATED APPLICATION

This application is a continuation-in-part of application Ser. No. 08/625,595, filed Apr. 3, 1996, now abandoned, and incorporated by reference.

FIELD OF THE INVENTION

The present invention relates to the encapsulation of cells in agarose and collagen, followed by coating with agarose, therapeutic methods employing the encapsulated cells, and manufacture thereof.

BACKGROUND AND PRIOR ART

The encapsulation of various biological materials in biologically compatible materials is a technique that has been used for some time, albeit with limited success. Exemplary of the art are U.S. Pat. Nos. 5,227,298 (Weber, et al); 5,053,332 (Cook, et al); 4,997,443 (Walthall, et al); 4,971,833 (Larsson, et al); 4,902,295 (Walthall, et al); 4,798,786 (Tice, et al); 4,673,566 (Goosen, et al); 4,647,536 (Mosbach, et al); 4,409,331 (Lim); 4,392,909 (Lim); 4,352,883 (Lim); and 4,663,286 (Tsang, et al). Also of interest is copending application Ser. No. 08/483,738, now U.S. Pat. No. 5,643,569 filed Jun. 7, 1995 to Jain, et al, incorporated by reference herein. Jain, et al discusses, in some detail, the encapsulation of secretory cells in various bio-compatible materials. As discussed therein, secretory cells are cells which secrete biological products. Generally, secretory cells possess at least some properties of endocrine cells, and may generally be treated as equivalent to cells which are endocrine in nature. The copending application discusses, e.g., the encapsulation of insulin producing cells, preferably in the form of islets, into agarose-collagen beads which have also been coated with agarose. The resulting products are useful in treating conditions where a subject needs insulin therapy, such as diabetes.

The Jain, et al application discusses, in some detail, the prior approaches taken by the art in transplantation therapy. These are summarized herein as well.

Five major approaches to protecting the transplanted tissue from the host's immune response are known. All involve attempts to isolate the transplanted tissue from the host's immune system. The immunoisolation techniques used to date include: extravascular diffusion chambers, intravascular diffusion chambers, intravascular ultrafiltration chambers, microencapsulation, and macroencapsulation. All of these methods have failed, however, due to one or more of the following problems: a host fibrotic response to the implant material, instability of the implant material, limited nutrient diffusion across semi-permeable membranes, secretagogue and product permeability, and diffusion lag-time across semi-permeable membrane barriers.

For example, a microencapsulation procedure for enclosing viable cells, tissues, and other labile membranes within a semipermeable membrane was developed by Lim in 1978. (Lim, Research report to Damon Corporation (1978)). Lim used microcapsules of alginate and poly L-lysine to encapsulate the islets of Langerhans. In 1980, the first successful in vivo application of this novel technique in diabetes research was reported (Lim, et al., Science 210: 908 (1980)). The implantation of these microencapsulated islets of Langerhans resulted in sustaining a euglycemic state in diabetic animals. Other investigators, however, repeating these experiments, found the alginate to cause a tissue reaction and were unable to reproduce Lim et al's results (Lamberti, et al. Applied Biochemistry and Biotechnology 10: 101 (1984); Dupuy, et al., J. Biomed. Material and Res. 22: 1061 (1988); Weber, et al., Transplantation 49: 396 (1990); and Doon-shiong, et al., Transplantation Proceedings 22: 754 (1990)). The water solubility of these polymers is now considered to be responsible for the limited stability and biocompatibility of these microcapsules in vivo (Dupuy, et al. supra, Weber et al. supra, Doon-shiong, et al., supra, and Smidsrod, Faraday Discussion of Chemical Society 57: 263 (1974)).

Recently, Iwata et al., (Iwata, et al. Jour. Biomedical Material and Res. 26: 967 (1992)) utilized agarose for microencapsulation of allogeneic pancreatic islets and discovered that it could be used as a medium for the preparation of microbeads. In their study, 1500–2000 islets were microencapsulated individually in 5% agarose and implanted into streptozotocin-induced diabetic mice. The graft survived for a long period of time, and the recipients maintained normoglycemia indefinitely.

Their method, however, suffers from a number of drawbacks. It is cumbersome and inaccurate. For example, many beads remain partially coated and several hundred beads of empty agarose form. Additional time is thus required to separate encapsulated islets from empty beads. Moreover, most of the implanted microbeads gather in the pelvic cavity, and a large number of islets are required in completely coated individual beads to achieve normoglycemia. Furthermore, the transplanted beads are difficult to retrieve, tend to be fragile, and will easily release islets upon slight damage.

A macroencapsulation procedure has also been tested. Macrocapsules of various different materials, such as poly-2-hydroxyethyl-methacrylate, polyvinylchloride-c-acrylic acid, and cellulose acetate were made for the immunoisolation of islets of Langerhans. (See Altman, et al., Diabetes 35: 625 (1986); Altman, et al., Transplantation: American Society of Artificial Internal Organs 30: 382 (1984); Ronel, et al., Jour. Biomedical Material Research 17: 855 (1983); Klomp, et al., Jour. Biomedical Material Research 17: 865–871 (1983)). In all these studies, only a transitory normalization of glycemia was achieved.

Archer et al., Journal of Surgical Research 28: 77 (1980), used acrylic copolymer hollow fibers to temporarily prevent rejection of islet xenografts. They reported long-term survival of dispersed neonatal murine pancreatic grafts in hollow fibers which were transplanted into diabetic hamsters. Recently Lacy et al., Science 254: 1782–1784 (1991) confirmed their results, but found the euglycemic state to be a transient phase. They found that when the islets are injected into the fiber, they aggregate within the hollow tube with resultant necrosis in the central portion of the islet masses. The central necrosis precluded prolongation of the graft. To solve this problem, they used alginate to disperse the islets in the fiber. However, this experiment has not been repeated extensively. Therefore, the membrane's function as an islet transplantation medium in humans is questionable.

Thus, there existed a need for achieving secretory cell transplantation, and, in particular, pancreatic islet allograft and xenograft survival without the use of chronic immunosuppressive agents.

In the Jain, et al work discussed supra, the inventors reported that encapsulating secretory cells in a hydrophilic gel material results in a functional, non-immunogenic material, that can be transplanted into animals and can be stored for long lengths of time. The encapsulation of the secretory cells provided a more effective and manageable technique for secretory cell transplantation. The encapsulation technique was described as being useful to encapsulate other biological agents, such as enzymes, micro-organisms, trophic agents including recombinantly produced trophic agents, cytotoxic agents, and chemotherapeutic agents. The encapsulated biological agents were discussed as being useful to treat conditions known to respond to the biological agent.

The application does not discuss at any length the incorporation of cells which produce diffusible biological materials, the latter being useful in a therapeutic context. A distinction is made herein between secretory cells and cells which produce diffusible biological materials. The former, as per the examples given in the Jain application, refers generally to products such as hormones, cell signalling agents, etc., which are normally considered to be biological "messengers". In contrast, diffusible biological materials refers to materials such as MHC presented peptides, cell expression regulators such as suppressors, promoters, inducers, and so forth. The distinction will be seen in the field of oncology, e.g., as per the following discussion.

Extensive studies in cancer have included work on heterogeneous cell extracts, and various cellular components. Via the use of monoclonal antibodies, the art has identified relevant cancer associated antigens, e.g., GM2, TF, STn, MUC-1, and various epitopes derived therefrom. Current theory postulates that epitopes derived from these various tumor markers complex noncovalently, with MHC molecules, thereby forming an agrotype by specific cytolytic T cells. This mechanism is not unlike various mechanisms involved in the biological response to viral infections. Note in this regard, Van der Bruggen, et al., *Science* 254: 1643–1647 (1991); Boon, et al., U.S. Pat. No. 5,405,940, and Boon, et al., U.S. Pat. No. 5,342,774, all of which are incorporated by reference.

Additional research which parallels the work on identification of so-called cancer epitopes has focused on the regulation of cancer proliferation, such as via suppression or, more generally, biomodulation. See, e.g., Mitchell, *J. Clin. Pharmacol* 32: 2–9 1992); Maclean, et al., *Can. J. Oncol.* 4: 249–254 (1994). The aim which unites all of these diverse approaches to cancer is the modification of the host's immune response, so as to bring about some improvement in the patient's condition.

Key to all of these approaches is the activity of one or more diffusible biological products which act in concert with other materials to modulate the immune response. Boon, et al. and van der Bruggen, et al., e.g., disclose small peptide molecules. Mitchell discusses larger molecules which function, e.g., as suppressors.

One problem with all therapeutic approaches which employ these materials is the delivery of these in a safe, effective form. This is not easily accomplished. It has now been found, surprisingly, that the techniques of Jain, et al, which were so useful in the development of therapies for conditions requiring secretory cell products can now be used in other areas.

How this is accomplished is the subject of the invention, the detailed description of which follows.

DETAILED DESCRIPTION OF PREFERRED EMBODIMENTS

EXAMPLE 1

This example, and those which follow, employ RENCA cells. These are spontaneous renal adenocarcinoma cells of BALB/C mice, which are widely available, having been maintained in both in vitro and in vivo cultures. See Franco et al., *Cytokine Induced Tumor Immunogenicity*, 181–193 (1994).

Samples of frozen RENCA cells were thawed at 37° C., and then placed in tissue culture flasks containing Dulbecco's Modified Medium (D-MEM), which had been supplemented with 10% bovine serum, penicillin (100 u/ml) and streptomycin (50 ug/ml), to give what will be refereed to as "complete medium" hereafter.

Cells were grown to confluency, and then trypsinized, followed by washing with Hank's Balanced Salt Solution, and then with the complete medium referred to supra.

In order to determine if the RENCA cells produced tumors efficiently, two BALB/C mice were injected, intraperitoneally, with $10^6$ of these cells. The mice were observed, over a 3–4 week period. Clinically, they appeared healthy for the first two weeks, and exhibited normal activity. Thereafter, the clinical manifestations of cancer became evident. One mouse died after 23 days, and the second, after 25 days. Following death, the mice were examined, and numerous tumors of various size were noted. Some of the tumors exhibited hemorrhaging as well.

A sample of one tumor, taken from one of the mice, was fixed in 10% formalin for later histological examination.

EXAMPLE 2

Following the showing that the RENCA cells did grow in vivo, studies were carried out to determine if these cells grew in beads in accordance with the invention.

RENCA cells were grown to confluency, as described supra, trypsinized, and washed, also as described above. Samples of between 60,000 and 90,000 cells were then prepared. The cells were then centrifuged, at 750 RPMs, and fluid was removed. The cells were then suspended in solutions of 1 atelocollagen, in phosphate buffered saline solution, at a pH of 6.5.

A 1% solution of low viscosity agarose was prepared in minimal essential medium (MEM), maintained at 60° C., and then 100 uls of this were added to the suspension of RENCA cells and atellocollagen, described supra. The materials were then transferred, immediately, as a single large droplet, into sterile, room temperature mineral oil. The mixture formed a single, smooth, semi-solid bead. This procedure was repeated to produce a number of beads.

After one minute the beads were transferred to complete medium, as described supra, at 37° C. The beads were then washed three times in minimal essential medium containing the antibiotics listed supra. The beads were then incubated overnight at 37° C., in a humidified atmosphere of air and 5% $CO_2$. Following the incubation, the beads, now solid, were transferred to a sterile spoon which contained 1 ml of 5% agarose in minimal essential medium. Beads were rolled in the solution 2–3 times to uniformly coat them with agarose. The beads were transferred to mineral oil before the agarose solidified, to yield a smooth outer surface. After 60 seconds, the beads were washed, five times, with complete medium at 37° C. to remove the oil. Overnight incubation (37° C., humidified atmosphere of air, 5% $CO_2$) followed.

These RENCA containing beads were used in the experiments which follow.

EXAMPLE 3

Prior to carrying out in vivo investigations, it was necessary to determine if the RENCA cells would grow in the beads prepared in the manner described supra.

To determine this, beads prepared as discussed in example 2 were incubated in the medium described in example 2, for a period of three weeks under the listed conditions. Three of the beads were then cut into small pieces, and cultured in standard culture flasks, affording direct contact with both the flask and culture medium.

Observation of these cultures indicated that the cells grew and formed standard RENCA colonies. This indicated that the cells had remained viable in the beads.

EXAMPLE 4

In vivo experiments were then carried out. In these experiments, the beads were incubated for seven days, at 37° C. Subject mice then received bead transplants. To do this, each of four mice received a midline incision, carried through intraperitoneally. Three beads, each of which contained 60,000 RENCA cells were transplanted. Incisions were then closed (two layer closure), using an absorbable suture. The four mice (BALB/C) were normal, male mice, weighing between 24–26 grams, and appeared to be healthy. Two sets of controls were set up. In the first set, two mice received three beads containing no RENCA cells, and in the second, two mice were untreated with anything.

Three weeks after the implantation, all of the mice received intraperitoneal injections of $10^6$ RENCA cells. Eighteen days later, one control mouse died. All remaining mice were then sacrificed, and observed.

Control mice showed numerous tumors, while the mice which received the implants of bead-encapsulated cells showed only random nodules throughout the cavity.

These encouraging results suggested the design of the experiments set forth in the following example.

EXAMPLE 5

In these experiments, established cancers were simulated by injecting RENCA cells under one kidney capsule of each of six BALB/C mice. Fifteen days later, mice were divided into two groups. The three mice in the first group each received three beads, as described in example 4, supra. The second group (the control group) received beads which did not contain RENCA cells.

After 4–5 days, mice which had received RENCA cell containing implants looked lethargic, and their fur had become spiky, while the control group remained energetic, with no change in condition of fur.

Ten days after implantation (25 days after injection of RENCA cells), however, the control mice became sluggish, and exhibited distended abdomens. One of the three control mice died at fourteen days following bead transplantation. Sacrifice of the mice followed.

The body cavities of the control mice showed profuse hemorrhaging, with numerous tumors all over the alimentary canal, liver, stomach and lungs. The entire abdominal cavity had become indistinguishable due to rampant tumor growth. The mice which had received beads with encapsulated RENCA cells, however showed no hemorrhaging, and only a few nodules on their alimentary canals. Comparison of test and control groups showed that, in the test group, nodules had not progressed.

EXAMPLE 6

Freely inoculated RENCA cell growth is inhibited when these cells are incubated along with encapsulated RENCA cells. A further set of experiments was carried out to determine if this effect was observable with other cells.

An adenocarcinoma cell line, i.e., MMT (mouse mammary tumor), was obtained from the American Type Culture Collection. Encapsulated MMT cells were prepared, as described, supra with MMT cells, to produce beads containing 120,000 or 240,000 cells per bead. Following preparation of the beads, they were used to determine if they would inhibit proliferation of RENCA cells in vitro. Specifically, two, six well petri plates were prepared, via inoculation with $1 \times 10^4$ RENCA cells per well, in 4 mls of medium. In each plate, three wells served as control, and three as test. One of the three control wells in each plate received one bead. Each of the other wells received either two or three empty beads. The second well was treated similarly, with wells receiving one, two or three beads containing 120,000 or 240,000 MMT cells. Wells were incubated at 37° C. for one week, after which RENCA cells were trypsinized, washed, and counted, using a hemocytometer. Results follow:

| Well # | DISH #1 (EMPTY MACROBEADS) # of cells retrieved after one week | | DISH #2 (MACROBEADS WITH MMT CELLS) # of cells retrieved after one week | |
|---|---|---|---|---|
| | Control | Empty | 120,000 MMT cells | 240,000 MMT cells |
| 1 | $2.4 \times 10^5$ | $2.8 \times 10^5$ | $1.4 \times 10^5$ | $1 \times 10^5$ |
| 2 | $2.0 \times 10^5$ | $3.6 \times 10^5$ | $1.2 \times 10^5$ | $7 \times 10^4$ |
| 3 | $4.4 \times 10^5$ | $2.5 \times 10^5$ | $1.25 \times 10^5$ | $9 \times 10^4$ |

EXAMPLE 7

Following the results in example 6, the same experiments was carried out, using $1 \times 10^4$ MMT cells rather than RENCA cells. The experiment was carried out precisely as example 6. Results are set forth below.

| Well # | Control | Empty Macrobeads | (1) MMT Macrobeads | (2) MMT Macrobeads |
|---|---|---|---|---|
| 1 | $3.1 \times 10^6$ | $2.8 \times 10^6$ | $1.6 \times 10^6$ | $1.3 \times 10^6$ |
| 2 | $3.3 \times 10^6$ | $2.6 \times 10^6$ | $1.0 \times 10^6$ | $1.1 \times 10^6$ |
| 3 | $3.0 \times 10^6$ | $2.8 \times 10^6$ | $6.0 \times 10^5$ | $5.0 \times 10^5$ |

These results encouraged the use of an in vivo experiment. This is presented in example 8.

EXAMPLE 8

RENCA cells, as used in the preceding examples, are renal cancer cells. To demonstrate more completely the general efficacy of the invention, work was carried out using a different type of cancer cells. Specifically, adenocarcinoma cells were used.

A mouse mammary tumor cell line (MMT) was obtained from the American Type Culture Collection. Using the protocols set forth, supra, implants were prepared which contained 120,000 cells per bead, and 240,000 cells per bead.

The experimental model used was the mouse model, supra. Twenty two mice were divided into groups of 4, 9 and 9. The first group, i.e., the controls, were further divided into three groups of two, one and one. The first subgroup received implants of one bead containing no cells. One mouse received two empty beads, and one received three empty beads.

Within experimental group A (9 animals), the beads contained 120,000 cells, while in group B, the beads contained 240,000 cells. Within groups "A" and "B", there were three subdivisions, each of which contained three mice. The subgroups received one, two, or three beads containing MMT cells.

Twenty one days following implantation, all animals received injections of 40,000 RENCA cells. Immediately after injection, the mice were lethargic, with spiky hair. This persisted for about five days, after which normal behavior was observed.

After twenty days, control mice exhibited distended abdomens, and extremely spiky hair. One control mouse died 25 days following injection, while the remaining control mice appeared terminal. All mice were sacrificed, and tumor development was observed. These observations are recorded infra:

| NUMBER OF MACROBEADS IN MICE | CONTROL | EXPERI- MENTAL GROUP A | EXPERI- MENTAL GROUP B |
|---|---|---|---|
| 1 | ++++ | − | − |
| 1 | ++++ | − | − |
| 1 |  | + | ++ |
| 2 | ++++ | − | − |
| 2 |  | − | − |
| 2 |  | ++ | ++ |
| 3 | ++++ | − | − |
| 3 |  | − | − |
| 3 |  | − | +++ |

These results show that, of eighteen mice tested, thirteen showed no disease. Of the mice in Group (A), one mouse exhibited a few modules, and another mouse showed a few tumors. One mouse which received two beads showed a few tumors.

Within group B, one mouse which had received one bead, and one mouse which received two beads showed a few tumors, entangled with intestines. One of the mice which received three beads had developed a large solid tumor and was apparently very sick. Nonetheless, the overall results showed that the encapsulated mouse mammary tumor cells inhibited tumor formation.

EXAMPLE 9

As suggested, supra, the practice of the invention results in the production of some material or factor which inhibits and/or prevents tumor cell proliferation. This was explored further in the experiment which follows.

Additional beads were made, as described supra in example 2, except that atelocollagen was not included. Hence, these beads are agarose/agarose beads. RENCA cells, as described, supra, were incorporated into these beads, again as described supra.

Two sets of three six well plates were then used as control, and experimental groups. In the control group, wells were filled with 4 ml of RPMI complete medium (10% fetal calf serum and 11 ml/l of penicillin). Each control group well was then inoculated with 10,000 RENCA cells.

In the experimental group, the RPMI complete medium was conditioned, by adding material secured by incubating 10 immunoisolated, RENCA containing beads (120,000 cell per bead), in a 35×100 mm petri plate containing 50 ml of the RPMI complete medium. Following five days of incubation, medium was collected from these plates, and 4 ml of it was placed in each test well. These wells were then inoculated with 10,000 RENCA cells.

All plates (both control and experimental) were incubated at 37° C. for five days. Following the incubation period cells were trypsinization washed, and counted using a hemocytometer. The cells in the plates of each well were pooled together following trypsinization, and counted, the results follow.

| WELL # | (CELLS) CONTROL | (CELLS) CONDITIONED |
|---|---|---|
| 1 | $7 \times 10^5$ | $3 \times 10^5$ |
| 2 | $8 \times 10^5$ | $2.5 \times 10^5$ |
| 3 | $7 \times 10^5$ | $3.4 \times 10^5$ |

These results show that the cells, when restricted in, e.g., the beads of the invention, produced some factor which resulted in suppression of tumor cell proliferation. This restriction inhibitor factor is produced by the cells in view of their entrapment in the bead, and differs from other materials such as contact inhibitor factor, which are produced when cells contact each other.

EXAMPLE 10

The experiment set forth supra showed that RENCA cell growth, in conditioned medium, was about half the growth of the cells in control medium. The experiments set forth herein examined whether the growth inhibiting factor would remain active after the conditioned medium was frozen.

RENCA conditioned medium was prepared by incubating 10 immunoisolated RENCA containing beads for five days. Incubation was in 35×100 mm petri plates, with 50 ml RMPI complete medium, at 37° C. Following the incubation, the medium was collected and stored at −20° C. Conditioned medium was prepared by incubating immunoisolated MMT (mouse mammary tumor) cell containing beads. The beads contained 240,000 cell per bead; otherwise all conditions were the same.

Frozen media were thawed at 37° C., and then used in the following tests. Three six well plates were used for each treatment, i.e., (i) RMPI control medium, (2) RENCA frozen conditioned medium, and (3) MMT frozen conditioned medium. A total of 4 ml of medium was dispensed into each well. All wells were then inoculated with 10,000 RENCA cells, and incubated at 37° C., for five days. Following incubation, two plates of samples were taken from each well, trypsinized, pooled, and counted in a hemocytometer. At eight days, the remaining three plates of each well were tested in the same way.

Results follow:

| DISH | CON- TROL MEDIUM | FROZEN CONDITIONED MEDIUM OF RENCA | FROZEN CONDITIONED MEDIUM OF MMT |
|---|---|---|---|
| 5 DAYS OLD |  |  |  |
| 1 | $6 \times 10^5$ | $5 \times 10^5$ | $8 \times 10^4$ |
| 2 | $6.8 \times 10^5$ | $4.2 \times 10^5$ | $8.5 \times 10^4$ |
| 8 DAYS OLD |  |  |  |
| 3 | $2.8 \times 10^6$ | $2 \times 10^6$ | $8 \times 10^4$ |

When these results are compared to those in example 6, supra, it will be seen that, while the frozen/thawed RENCA conditioned medium did not arrest growth to the same extent that unfrozen medium did (compare examples 6 and 7), it did, nonetheless, arrest growth). Frozen conditioned medium using MMT cells arrested growth even more than the unfrozen MMT conditioned medium. These results show that, of eighteeen mice tested, thirteen showed no disease. Of the mice in Group (A), one mouse exhibited a few modules, and another mouse showed a few tumors.

The foregoing describes the manufacture of implantable beads which contain one or more types of cells which produce a diffusible biological product, as this phrase is defined herein. The, diffusible biological product is one which has an effect on the subject in which the bead is implanted. Preferably, this effect is immunomodulation, such as stimulating an immune response, or suppressing a response. In the case of cancer, for example, the diffusible biological product may be a peptide which complexes with MHC molecules on cancer cells in a subject, thereby provoking a CTL response thereto in turn leading to lowering of the tumor load in the subject. The diffusible product may also be a suppressor of tumor growth. In connection with this form of therapy, it is possible, although not necessarily preferable, to place the implanted beads in or near an identified tumor.

"Diffusible biological product" as used herein refers to materials such as proteins, glycoproteins, lipoproteins, carbohydrates, lipids, glycolipids, and peptides. More specifically, materials such as antibodies, cytokines, hormones, enzymes, and so forth, are exemplary, but by no means the only type of materials included. Excluded are the well known "end products" of cellular processes, such as $CO_2$ and $H_2O$.

As the experiments show, the implantable beads may also be used prophylactically. It is well known that at least a segment of the population of cancer patients are prone to re-occurrence of the condition. The experiments described herein show that the o implants can prevent the occurrence or reoccurrence of cancer, via the biological effect the diffusible product has on a subject's system.

The discussion of the invention has focused on in vivo approaches. It must also be understood that there are in vitro approaches to the invention, some of which are elaborated upon herein. For example, it is well known that many cells which produce desirable products, when cultured in vitro, require the presence of feeder cells. There are always issues with such feeder cells. They may grow faster than the desired cells, leading to de facto "strangulation" of the materials of interest. Further, there can be a problem with various toxic products being produced by the feeder layers. The implantable beads of the invention act almost as cellular incubators, protecting the incorporated cells, while permitting the diffusible products to move into a culture medium, e.g., where they can be collected.

As indicated, supra, preparation of the implantable beads first requires suspension of the cells in solution, preferably aqueous of collagen. Preferably, the collagen is atelocollagen, in a solution of from about 0.5 to about 2%. Depending upon the type of cell used, the number of cells in the solution at a given time, and hence the number of cells in a bead, will vary. Preferably, there are from about 10,000 to about 200,000 cells used per bead, more preferably from about 30,000 to about 100,000. Most preferably, about 40,000 to about 60,000 cells are used.

Following suspension of the cells in the collagen solution, an agarose solution is added. Preferably, this agarose solution will range from about 0.5% to about 5%, preferably about 1%. By dropping the mixture onto or into inert materials, such as TEFLON® or mineral oil, a bead forms. This bead is semi-solid. The semi-solid bead is then transferred to a sterile medium, preferably one containing antibiotics, washed, and incubated to polymerize collagen. The polymerization of collagen is a well studied phenomenon, and the conditions under which this occurs need not be elaborated upon herein.

Following the solidification of the bead, it is then coated with agarose, preferably by rolling it in an agarose solution. One preferred way of accomplishing this is a simple TEFLON® coated spoon which contains a solution of agarose, preferably 5 to 10%.

The foregoing discussion of diffusible biological products should not be construed as being limited to wild type materials. For example, one can just as easily incorporate transformed or transfected host cells, such as eukaryotic cells (e.g., 293 cells, CHO cells, COS cells), or even prokaryotic cells (e.g., *E. coli*), which have been treated to produce heterogeneous protein, or modified via, e.g., homologous recombination, to produce increased amounts of desirable biological products, Other materials, such as hybridomas, may also be used, with the diffusible biological product being a monoclonal antibody.

Other features and aspects of the invention will be clear to the skilled artisan, and need not be related here.

The terms and expression which have been employed are used as terms of description and not of limitation, and there is no intention in the use of such terms and expression of excluding any equivalents of the features shown and described or portions thereof, it being recognized that various modifications are possible within the scope of the invention.

We claim:

1. A composition of matter comprising a solid, agarose coated, agarose containing bead, wherein said bead contains cancer cells isolated from an animal which, when restricted by being entrapped in said bead, produce more of a material that suppresses cancer cell proliferation, wherein said material diffuses through said solid, agarose coated, agarose containing bead.

2. The composition of matter of claim 1, wherein said cancer cells are renal cancer cells.

3. The composition of matter of claim 1, wherein said bead contains from about 10,000 to about 200,000 cells.

4. The composition of matter of claim 3, wherein said bead contains from about 30,000 to about 100,000 cells.

5. Method for suppressing cancer cell proliferation in a subject, comprising implanting a sufficient amount of the composition of matter of claim 1 in said subject to suppress the proliferation of cancer cells in subject.

6. A process for making a solid bead which comprises agarose, and is coated with agarose, wherein said solid bead contains cancer cells which, when restricted by being entrapped in said bead produce material that suppresses cancer cell proliferation and diffuses through said bead, comprising:

(a) adding agarose to a solution which contains a sample of cancer cells isolated from an animal which are capable of producing material that suppresses cancer cell proliferation which diffuses through said bead when said cancer cells are restricted by being entrapped by the bead, (b) forming a semi-solid bead comprising said agarose and said cancer cells, (c) polymerizing the agarose in said semi-solid bead to form a solid, agarose bead containing and thereby restricting said cancer cells, and (d) coating said solid, agarose containing bead containing the restricted cancer cells with agarose, wherein said restricted cancer cells produce more of said material than when said cancer cells are not entrapped in said bead.

7. The process of claim 6, wherein said solution contains from about 10,000 to about 200,000 cells.

8. The process of claim 6, wherein said solution contains from about 30,000 cells to about 100,000 cells.

* * * * *